United States Patent [19]

Bennett et al.

[11] 4,179,936

[45] Dec. 25, 1979

[54] ACOUSTIC IMAGE RECORDERS

[75] Inventors: Simon D. Bennett; Eric A. Ash, both of London, England

[73] Assignee: National Research Development Corporation, London, England

[21] Appl. No.: 907,320

[22] Filed: May 18, 1978

[30] Foreign Application Priority Data

May 17, 1977 [GB] United Kingdom ............... 20712/77

[51] Int. Cl.$^2$ .......................................... G01N 29/00
[52] U.S. Cl. ...................................................... 73/606
[58] Field of Search ................. 73/596, 599, 602, 617, 73/620, 624, 627, 606, 642, 644; 340/5 MP

[56] References Cited

U.S. PATENT DOCUMENTS

| 3,986,160 | 10/1976 | Turner ............................. 73/617 X |
| 4,012,950 | 3/1977 | Kompfner et al. ..................... 73/596 |
| 4,028,933 | 6/1977 | Lemons et al. ......................... 73/627 |
| 4,030,342 | 6/1977 | Bond et al. . |

*Primary Examiner*—Charles A. Ruehl

*Attorney, Agent, or Firm*—Cushman, Darby & Cushman

[57] ABSTRACT

A method of sensing changes in an object comprising irradiating the object with a focused beam of acoustic radiation excited by a first alternating electric signal; receiving a beam of acoustic radiation modulated in phase and amplitude by the object in the vicinity of the focus and deriving a second alternating electric signal therefrom; providing a reference electric signal derived from the first alternating electric signal and at a known phase; mixing coherently the second signal and the reference signal to derive a first in-phase signal; mixing the second signal with the reference signal altered in phase by between 80° and 100° to provide a first quadrature signal; storing the first in-phase and first quadrature signals; after an interval of time receiving a beam of acoustic radiation modulated by the same part of the object and deriving a third alternating electric signal therefrom and similarly deriving second in-phase and second quadrature signals; and combining the stored first and the second signals so as to sense any change in the object.

12 Claims, 2 Drawing Figures

U.S. Patent        Dec. 25, 1979        4,179,936
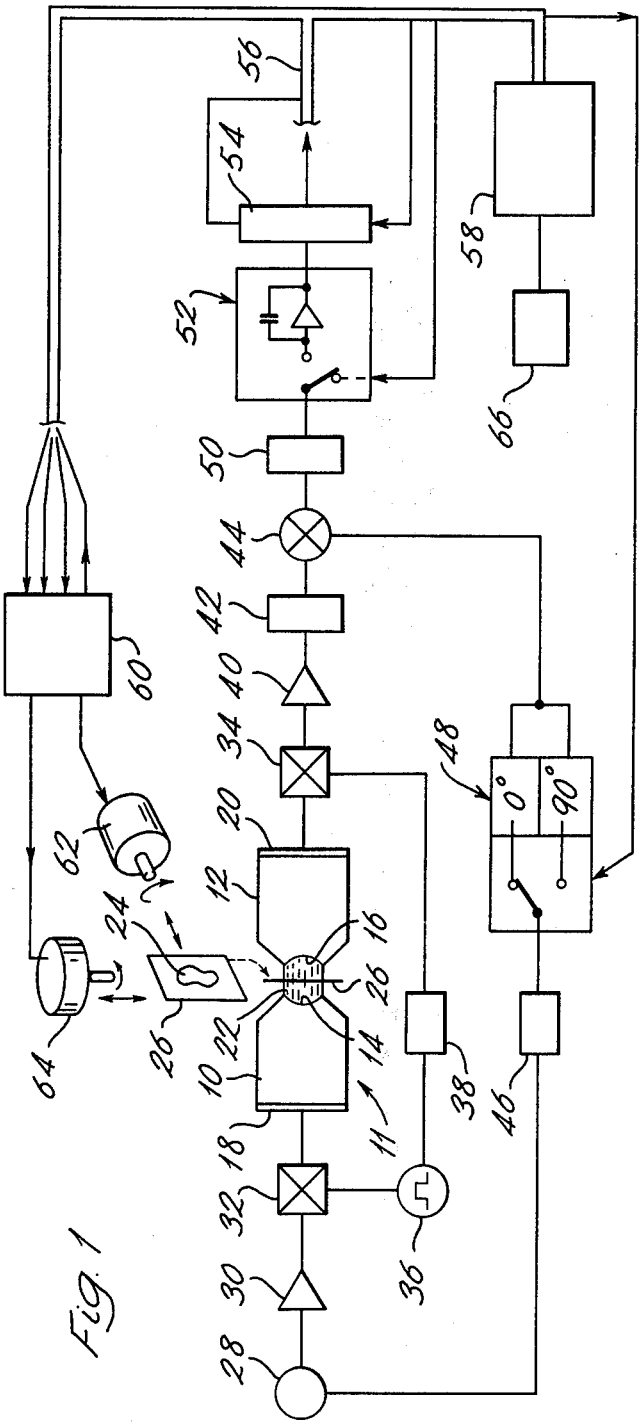
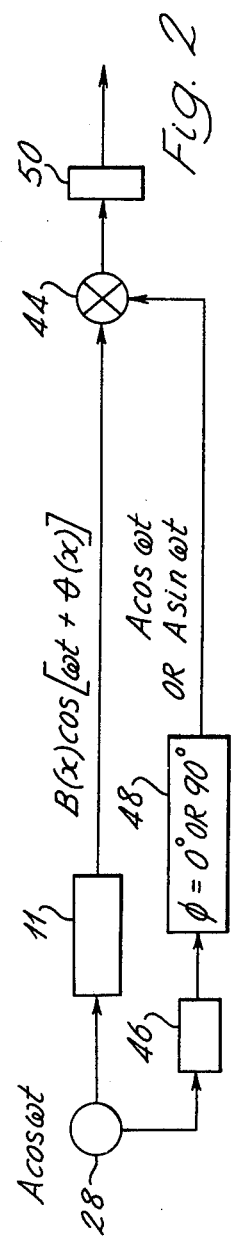

ACOUSTIC IMAGE RECORDERS

This invention relates to acoustic image recorders.

In the field of microscopy, a very recent development is the use of acoustic radiation to 'view' an object; an acoustic wave is focused in a water cell by a suitably-shaped acoustic lens, a specimen is scanned mechanically through the focus, and acoustic radiation modulated by passage through the specimen is received by another acoustic lens. Such an arrangement is described by R. A. Lemons and C. F. Quate in the 1973 Ultrasonics Symposium Proceedings of the Institute of Electrical and Electronic Engineers, Cat. #73 CHO 807-8SU, in a paper entitled "A Scanning Acoustic Microscope."

Such a device can be used to provide information about the specimen at a very large number of points spaced on or under its surface. In interpreting this information, it may be useful to consider only changes in the specimen which have occurred since a previous record was obtained; the changes may occur in amplitude or in phase or in both. While previous arrangements have been capable of providing an image using only phase contrast or only amplitude contrast or using a known or unknown combination of the two, it is believed that it has not previously been possible to record simultaneous changes in both variables after the elapse of period of time.

According to the invention a method of sensing changes in an object comprises irradiating the object with a focused beam of acoustic radiation excited by a first alternating electric signal; receiving a beam of acoustic radiation modulated in phase and amplitude by the object in the vicinity of the focus and deriving a second alternating electric signal therefrom; providing a reference signal derived from the first alternating electric signal and at a known phase; mixing coherently the second signal and the reference signal to derive a first in-phase signal; mixing the second signal with the reference signal altered in phase by between 80° and 100°, conveniently 90°, to provide a first quadrature signal; storing the first in-phase and first quadrature signals; after an interval of time receiving a beam of acoustic radiation modulated by the same part of the object and deriving a third alternating electric signal therefrom and similarly deriving second in-phase and second quadrature signals; and combining the stored first and the second signals so as to sense any change in the object.

The beam of acoustic radiation may be either transmitted through or reflected by the object.

The stored first and the second signals may be combined by simple addition or simple subtraction, or by addition or subtraction after multiplication of one signal by a constant factor, or by other mathematical operations.

Usually the method will further comprise causing relative movement in the focal plane of the object and the focus of the acoustic beam, deriving a first in-phase and a first quadrature signal at each of a plurality of relative positions; storing each first in-phase and first quadrature signal; after said interval of time repeating the movement and deriving a second in-phase and a second quadrature signal at each said position; and combining for each position the stored first and the second signals.

Also according to the invention, apparatus for sensing a change in an object comprises means for irradiating the object with a focused beam of acoustic radiation excited by a first alternating electric signal; means for receiving a beam of acoustic radiation modulated in phase and amplitude by the object in the vicinity of the focus and for deriving a second alternating electric signal therefrom; means for providing a reference signal derived from the first alternating electric signal and at a known phase; and mixing means for mixing coherently the second signal and the reference signal to derive an in-phase signal and for mixing the second signal and the reference signal altered in phase by between 80° and 100° to derive a quadrature signal.

In one arrangement of the apparatus there are further provided scanning means arranged to move the object stepwise with respect to the focus of the acoustic beam in the focal plane and in a repeatable pattern; storage means connected to the mixing means to store an in-phase signal and a quadrature signal corresponding to each relative position of the object; and combination means arranged to combine for each position of the object the stored signal with the successively provided signal.

The invention will now be described by way of example with reference to the accompanying drawings in which:

FIG. 1 is a block diagram of apparatus according to the invention; and

FIG. 2 is a simplified block diagram of part of the apparatus indicating the electrical signals and their combination.

In FIG. 1, a scanning transmission acoustic microscope 11 comprises first and second sapphire crystals 10, 12, each having a polished spherical concave surface 14, 16 and an opposite plane surface with which a piezo electric transducer 18, 20 is in contact. The concave surfaces are arranged adjacent each other; each may have a radius of curvature of about 0.13 millimeters and a drop of water 22 is held between them by surface tension.

If an alternating voltage is applied to the transducer 18, a plane wave of acoustic radiation will be generated and will pass through the crystal 10 into the water drop 22; the curved surface 14 will focus the beam in the water. If a thin sample 24 attached to a polyethyleneterephthalate film 26 is placed at the focus, the specimen will modulate acoustic radiation passing through it, and, if the concave surfaces 14, 16 are arranged confocally, the crystal 12 will receive the radiation from the focus and provide a related a.c. signal at the transducer 20. If the specimen is scanned through the focus, for example in a raster pattern, a picture may be built up point-by-point from the signal at transducer 20. This is the basic scanning acoustic microscope described by Lemons and Quate and referred to above.

In order to allow a change in an object to be recorded, additional apparatus is required. The transducer 18 is supplied by a 1 GHz oscillator 28 through an amplifier 30 and switch 32, and the transducer 20 is connected to a switch 34. The switches 32, 34 are controlled by a pulse generator 36, the switch 34 being operated through a delay line 38 to allow for the time of passage of acoustic radiation through the microscope. The switches 32, 34 allow the technique of time gating to be used to allow passage through the switch 34 only of required signals, i.e. signals corresponding to the direct passage of acoustic radiation through the microscope; signals corresponding to acoustic radiation reflected at the curved surfaces 14, 16 are rejected.

The switch 34 is connected through an amplifier 40 and bandpass filter 42 to the first input of a mixer 44; the second input of the mixer is supplied from the oscillator 28 through a delay line 46 and a switchable phase shifter 48. The mixer output is connected to a low pass filter 50.

In use, the delay line 46 introduces a delay approximately equal to the time of passage of acoustic radiation through the microscope, which greatly reduces the effect of any short-term oscillator instability. The low pass filter 50 provides suppression of unwanted modulation products; its time constant is selected to effectively integrate the detected signal pulse.

In the following description, the apparatus is arranged so that the combination of the delay line 46 and the switchable phase shifter 48 provide at the input to the mixer 44 a signal which is either in phase or in phase quadrature with the output signal which the microscope would provide in the absence of any object, i.e. the phase of the directly transmitted first alternating electric signal.

The mixer then combines two signals which are either precisely in phase, to give an in-phase signal, or which differ in phase by 90°, to give a phase quadrature signal. This allows a clear explanation of the invention using simple mathematics.

However, the conditions are not essential. So long as the two phases provided through the phase shifter are always the same, and differ by 90°, then two signals, nominally "in-phase" and "quadrature," can be derived, and phase changes in the object can be detected. The actual phases of the two signals must be known, and one can be chosen as an arbitrary origin to give the "in-phase" signal.

Further, the phase shifter need not alter the phase by precisely 90° to give the quadrature signal; phase shifts of between 80° and 100° can be applied; the actual shift must be precisely determined by a calibration procedure, and a simple first order numerical correction applied to the output data.

Probably a phase difference between the "in-phase" and "quadrature" signals much lower than 80° will allow phase changes in the object to be detected, so long as the magnitude is accurately known, but greater corrections will then need to be applied to the data.

Referring now to FIG. 2, suppose the oscillator output, (the first alternating electric signal), is $A\cos\omega t$. In the absence of the specimen 24 and with the phase shifter 48 set to zero phase shift, the delay line 46 is chosen or set so that the inputs to the mixer 44 from the phase shifter 48 (the reference signal) and from the microscope 11 through the switch 34 (the second alternating electric signal) are in phase and can therefore both be considered to be $A\cos\omega t$ since the actual phase retardations are equal in value. If the phase shifter 48 is altered to a shift of 90°, the input to the mixer 44 from the phase shifter can be considered to be $A\sin\omega t$. Suppose the transmission function of the specimen 24 is $B(x)\angle\theta°$, that is, an amplitude component $B(x)$ and an associated phase shift of $\theta°$; the output signal of the microscope 11 is then $B(x)\cos[\omega t + \theta(x)]$ if a constant factor is ignored; this signal is supplied to the first input of the mixer 44.

The output of the mixer 44 is the product of the two input signals:

when $\phi = 0$,
$$\text{output} = A\cos\omega t \times B(x)\cos[\omega t + \theta(x)]$$

-continued
$$= \frac{AB(x)}{2}\{\cos\theta(x) + \cos[2\omega t + \theta(x)]\}$$

the low pass filter 50 allows passage of the signal:

$$\frac{AB(x)}{2}\cos\theta(x). \quad (1)$$

when $\phi = 90°$,
$$\text{output} = A\sin\omega t \times B(x)\cos[\omega t + \theta(x)]$$
$$= \frac{AB(x)}{2}\{-\sin\theta(x) + \sin[2\omega t + \theta(x)]\}$$

The low pass filter 50 allows passage of the signal:

$$\frac{AB(x)}{2}\sin\theta(x). \quad (2)$$

The measurement of the two quantities represented by the expressions (1) and (2) allows the separate determination of $B(x)$ and of $\theta(x)$.

Consider now one point in the object at the position $(i\delta x, j\delta y)$ where $\delta x.\delta y$ is the dimension of the picture element and i and j are integers; let the complex amplitude be $B_{ij}$ before an alteration in the object and $C_{ij}$ after the alteration. If records are made of $B_{ij}$ and $C_{ij}$, they can be combined in several ways. For example, $B_{ij}-C_{ij}$ will contain all the information on the alteration, and can be displayed suitably. Alternatively, if $B_{ij}+K\,C_{ij}$ is displayed, where K is a complex constant, then $B_{ij}$ provides a reference background of the original image and superimposition of $K\,C_{ij}$ results in interference fringes similar to those familiar in optical metrology. These fringes can be regarded as scaled contours of the alteration. If the variation is predominantly in amplitude, then a display of $B_{ij}+C_{ij}C_{ij}^*$ could be provided, where $C_{ij}^*$ is the complex conjugate of $C_{ij}$. Other mathematical operations are also possible.

Referring again to FIG. 1, suppose the object 26 is scanned stepwise in a raster pattern and the output of the mixer 44 is recorded for every point on the pattern, both when the phase shifter 48 introduces zero phase shift and when it introduces a 90° phase shift. The object is then altered or allowed to alter in some way and is scanned again in exactly the same raster pattern, a record being made for $\theta = 0$ and $\theta = 90°$ at every point. The two records then comprise $B_{ij}$ and $C_{ij}$ and can be combined in any way by provision of suitable digital processing, operating in a conventional manner. It is an advantage of the invention that the most suitable form of display can be selected easily.

Apparatus for controlling the production of the records $B_{ij}$ and $C_{ij}$ will now be described with reference to FIG. 1.

The low pass filter 50 is connected through a sample and hold unit 52 and an analogue-to-digital converter 54 via a control line system 56 to a control and memory circuit 58 and also to a stepper motor drive and control circuit 60. The circuit 60 controls two stepper motors 62, 64 which control the position of the film 26 to which the object 24 is attached. The circuit 60 is also connected to a display unit 66, such as a cathode ray tube.

The control circuit 58 also controls operation of the sample-and-hold unit 52, the A/D converter 54 and the switchable phase shifter 48.

A typical cycle under the control of the control circit 58 to produce the records of the signal $B_{ij}$ and $C_{ij}$ could be as follows:

1. The phase shifter 48 is set to $\theta=0$.
2. The stepper motors 62, 64 are commanded to move to a given location, the point i$\delta$x, j$\delta$y, and to stop at that point.
3. After a short delay to allow the system to settle, the sample-and-hold circuit 52 is set to hold the analogue signal level on its input. This corresponds to the output signal from the microscope 11 which is focused on the point i$\delta$x, j$\delta$y, and is $A_{ij} \cos \phi$ ij.
4. A fixed signal level corresponding to $A_{ij} \cos \phi_{ij}$ appears at the input of the A/D converter 54.
5. The converter 54 passes a digital signal to the memory part of the control circuit 58, and the sample-and-hold circuit is then allowed to follow the input signal again.
6. The phase shifter 48 is set to $\phi=90°$. Steps 3, 4 and 5 are repeated and a digital signal corresponding to $A_{ij} \sin \phi_{ij}$ is stored in the memory circuit.
7. The stepper motors move the object to a new position and the measurement cycle is repeated.

After the object has been scanned in a raster pattern, the object is changed or allowed to change. The cycle is then repeated with the object scanned in precisely the same pattern. The first and second records $B_{ij}$ and $C_{ij}$ are then combined by the memory circuit in the required manner and displayed.

It is to be understood that many modification may be made to the apparatus. For example, if a sufficiently stable oscillator is used, the delay line 46 need not provide a time delay equal to the time of passage of the acoustic wave through the microscope, but need provide only a much smaller phase shift so that the reference signal is at the required phase. It will be understood that there is an important distinction between the function of the delay line 46 and the phase shifter 48 despite the fact that both introduce phase changes. The object of the 90° phase shift provided by the phase shifter 48 is to provide a quadrature reference signal; its absolute phase relative to the signal path through the microscope is arbitrary—the essential point is that there is a phase difference of 90° between the two possible reference signals. Either the input oscillator is phase stable over the period of signal transit through the microscope, or a delay line 46 is required. The effect of the delay device, when the delay is approximately equal to the transit time of the signal through the micrscope, is to "remember" the phase at the instant of transmission. Thus the use of a delay line 46 allows a relaxation of the tolerance on oscillator stability.

Other modifications are possible; if the microscope is arranged so that there are no reflections of acoustic radiation, the received signal need not be pulse-gated; the phase and amplitude signals for each position may be derived simultaneously instead of successively, when the scanning movement need not be incremental but can be continuous; the acoustic microscope need not comprise sapphire crystals having concave faces but may take the form described in our co-pending British Patent application No. 20713/77 filed on even date.

Further, a reflection mode of microscope operation may be used instead of the transmission mode described above.

Examples of types of alterations in the object which may be observed by a method and apparatus according to the invention include the measurement of dimensional changes, measurement of changes in physical properties such as viscosity and elasticity, changes arising from biological processes such as cell growth and division, and observation of crystal growth.

We claim:

1. A method of sensing changes in an object comprising irradiating the object with a focused beam of acoustic radiation excited by a first alternating electric signal; receiving a beam of acoustic radiation modulated in phase and amplitude by the object in the vicinity of the focus and deriving a second alternating electric signal therefrom; providing a reference electric signal derived from the first alternating electric signal and at a known phase; mixing coherently the second signal and the reference signal to derive a first in-phase signal; mixing the second signal with the reference signal altered in phase by between 80° and 100° to provide a first quadrature signal; storing the first in-phase and first quadrature signals; after an interval of time receiving a beam of acoustic radiation modulated by the same part of the object and deriving a third alternating electric signal therefrom and similarly deriving second in-phase and second quadrature signals; and combining the stored first and the second signals so as to sense any change in the object.

2. A method according to claim 1 in which the beam of acoustic radiation is transmitted through the object.

3. A method according to claim 1 in which the beam of acoustic radiation is reflected by the object.

4. A method according to claim 1 further comprising causing relative movement in the focal plane of the object and the focus of the acoustic beam; deriving a first in-phase and a first quadrature signal at each of a plurality of relative positions; storing each first in-phase and first quadrature signal; after said interval of time repeating the movement and deriving a second in-phase and a second quadrature signal at each said position; and combining for each position the stored first and the second signals.

5. Apparatus for use in sensing a change in an object comprising means for irradiating the object with a focused beam of acoustic radiation excited by a first alternating electric signal; means for receiving a beam of acoustic radiation modulated in phase and amplitude by the object in the vicinity of the focus and for deriving a second alternating electric signal therefrom; means for providing a reference electric signal derived from the first alternating electric signal and at a known phase; and mixing means for mixing coherently the second signal and the reference signal to derive an in-phase signal and for mixing the second signal and the reference signal altered in phase by between 80° and 100° to derive a quadrature signal.

6. Apparatus according to claim 5 further comprising scanning means arranged to cause relative movement in the focal plane of the object and the focus of the acoustic beam; storage means connected to the mixing means to store an in-phase signal and a quadrature signal corresponding to each of a plurality of relative positions of the object; and combination means for combining for each position of the object the stored signals with the successively provided signals.

7. Apparatus according to claim 6 in which the scanning means moves the object stepwise in the focal plane in a repeatable pattern; and at each step in the movement an in-phase and a quadrature signal are derived.

8. Apparatus for sensing changes in an object comprising:

means for irradiating the object with a focused beam of acoustic radiation excited by a first alternating electric signal;

means for receiving a beam of acoustic radiation modulated in phase and amplitude by the object in the vicinity of the focus and deriving a second alternating electric signal therefrom;

means for providing a reference electric signal derived from the first alternating electric signal and at a known phase;

means for mixing coherently the second signal and the reference signal to derive a first in-phase signal;

means for mixing the second signal with the reference signal altered in phase by between 80° and 100° to provide a first quadrature signal;

means for storing the first in-phase and first quadrature signals;

means operative after an interval of time for receiving a beam of acoustic radiation modulated by the same part of the object and deriving a third alternating electric signal therefrom and similarly deriving second in-phase and second quadrature signals; and means for combining the stored first and the second signals so as to sense any change in the object.

9. Apparatus according to claim 8 further comprising:

means for causing relative movement in the focal plane of the object and the focus of the acoustic beam;

means for deriving a first in-phase and a first quadrature signal at each of a plurality of relative positions;

means for storing each first in-phase and first quadrature signal;

means operative after said interval of time for repeating the movement and deriving a second in-phase and a second quadrature signal at each said position; and means for combining for each position the stored first and the second signals.

10. A method for sensing change in an object comprising:

irradiating the object with a focused beam of acoustic radiation excited by a first alternating electric signal;

receiving a beam of acoustic radiation modulated in phase and amplitude by the object in the vicinity of the focus and for deriving a second alternating electric signal therefrom;

providing a reference electric signal derived from the first alternating electric signal and at a known phase;

mixing coherently the second signal and the reference signal to derive an in-phase signal; and mixing the second signal and the reference signal altered in phase by between 80° and 100° to derive a quadrature signal.

11. A method according to claim 10 further comprising:

scanning to cause relative movement in the focal plane of the object and the focus of the acoustic beam;

storing an in-phase signal and a quadrature signal corresponding to each of a plurality of relative positions of the object; and combining for each position of the object the stored signals with the successively provided signals.

12. A method according to claim 11 in which the said scanning includes moving the object stepwise in the focal plane in a repeatable pattern and said method includes deriving at each step in the movement an in-phase and a quadrature signal.

* * * * *

UNITED STATES PATENT AND TRADEMARK OFFICE
CERTIFICATE OF CORRECTION

PATENT NO. : 4,179,936

DATED : December 25, 1979

INVENTOR(S) : Simon D. BENNETT and Eric A. ASH

It is certified that error appears in the above—identified patent and that said Letters Patent is hereby corrected as shown below:

In the heading

Please delete:

[30]  Foreign Application Priority Data

May 17, 1977 [GB] United Kingdom.....20712/77

Signed and Sealed this

Tenth Day of June 1980

[SEAL]

Attest:

SIDNEY A. DIAMOND

Attesting Officer     Commissioner of Patents and Trademarks